(12) United States Patent
Correale

(10) Patent No.: US 8,237,116 B2
(45) Date of Patent: Aug. 7, 2012

(54) GC-MS ANALYSIS APPARATUS

(75) Inventor: Raffaele Correale, Turin (IT)

(73) Assignee: Agilent Technologies, Inc., Santa Clara, CA (US)

( * ) Notice: Subject to any disclaimer, the term of this patent is extended or adjusted under 35 U.S.C. 154(b) by 55 days.

(21) Appl. No.: 12/831,921

(22) Filed: Jul. 7, 2010

(65) Prior Publication Data

US 2011/0006201 A1    Jan. 13, 2011

(30) Foreign Application Priority Data

Jul. 8, 2009   (IT) .............................. TO2009A0513
May 13, 2010  (IT) .............................. TO2010A0399

(51) Int. Cl.
    *B01D 59/44* (2006.01)
(52) U.S. Cl. ........ 250/288; 250/281; 250/282; 250/289; 73/23.2; 73/23.22; 73/23.35; 73/23.37; 96/4; 96/106
(58) Field of Classification Search ................ 250/281, 250/282, 283, 288, 289; 73/23.2, 23.22, 73/3.27, 23.35, 23.37, 23.42; 96/4, 106
    See application file for complete search history.

(56) References Cited

U.S. PATENT DOCUMENTS

| | | | |
|---|---|---|---|
| 3,455,902 A | | 7/1969 | Llewellyn |
| 3,712,111 A | * | 1/1973 | Llewellyn .................... 73/23.37 |
| 3,751,880 A | * | 8/1973 | Holm ................................. 96/5 |
| 4,008,388 A | * | 2/1977 | McLafferty et al. ............ 702/27 |
| 4,051,372 A | * | 9/1977 | Aine ............................ 250/343 |
| 4,311,669 A | | 1/1982 | Spangler |
| 4,551,624 A | | 11/1985 | Spangler et al. |
| 4,712,008 A | | 12/1987 | Vora et al. |
| 4,804,839 A | | 2/1989 | Broadbent et al. |
| 6,006,584 A | | 12/1999 | Itoi |
| 6,039,792 A | | 3/2000 | Calamur et al. |
| 6,822,226 B2 | | 11/2004 | Ross et al. |
| 7,037,425 B2 | | 5/2006 | Lee et al. |
| 7,217,919 B2 | * | 5/2007 | Boyle et al. .................... 250/285 |
| 7,361,888 B1 | * | 4/2008 | Boyle et al. .................... 250/285 |
| 7,528,366 B1 | * | 5/2009 | Boyle et al. .................... 250/285 |
| 7,582,867 B2 | | 9/2009 | Wells et al. |
| 7,690,241 B2 | | 4/2010 | Taylor et al. |

(Continued)

FOREIGN PATENT DOCUMENTS

EP        1764823 A2      3/2007

(Continued)

OTHER PUBLICATIONS

Maden, A. M. et al., "Sheet Materials for Use as Membranes in Membrane Introduction Mass Spectometry", Analytical Chemistry, American Chemical Society, May 15, 1996, vol. 68 No. 10, pp. 1805-1811, US.

(Continued)

*Primary Examiner* — Bernard E Souw

(57) ABSTRACT

GC-MS analysis apparatus has an interface section between GC and MS sections, which is located with respect to the direction of an analyte flow downstream of the GC section and upstream of the MS section. The interface section comprises at least one membrane with at least one orifice capable of establishing a molecular flow condition in the analyte passing between the GC and MS sections through the membrane. The membrane is subjected to a pressure differential such that the pressure $p_a$ in a region located upstream of the membrane is higher than the pressure $p_b$ in a region located downstream of the membrane.

15 Claims, 6 Drawing Sheets

U.S. PATENT DOCUMENTS

| | | |
|---|---|---|
| 7,803,274 B2 | 9/2010 | Taylor et al. |
| 2002/0134933 A1 | 9/2002 | Jenkins et al. |
| 2006/0091308 A1* | 5/2006 | Boyle et al. .................. 250/285 |
| 2009/0294657 A1 | 12/2009 | Rafferty |
| 2010/0223979 A1* | 9/2010 | Ploehn et al. .................... 73/38 |

FOREIGN PATENT DOCUMENTS

| | | |
|---|---|---|
| JP | 2001-155677 A1 | 6/2001 |
| WO | 01/35441 A1 | 5/2001 |
| WO | 03/049840 A1 | 6/2003 |
| WO | 2008/074984 A1 | 6/2008 |

OTHER PUBLICATIONS

European Patent Office, Communication dated Aug. 18, 2010.
Office Action mailed Mar. 2, 2012 in co-pending U.S. Appl. No. 12/831,945 filed Jul. 7, 2010.

* cited by examiner

US 8,237,116 B2

GC-MS ANALYSIS APPARATUS

CROSS REFERENCE TO RELATED APPLICATIONS

This patent application claims the benefit of the Italian priority patent application no. TO2009A000513 filed on Jul. 8, 2009, and also claims further priority to the subsequently filed Italian patent application no. TO2010A000399 filed on May 13, 2010. This patent application relates to the U.S. patent application filed on Jul. 7, 2010, which is presently identified and is titled "GAS SAMPLING DEVICE AND GAS ANALYZER EMPLOYING THE SAME".

TECHNICAL FIELD

The present invention relates to a GC-MS apparatus, the apparatus for the analysis of volatile substances, or substances that can be made volatile, which is based on the combination of gas chromatography (GC) technique and mass spectrometry (MS).

BACKGROUND OF THE INVENTION

Gas chromatography is often used in order to separate mixtures of substances, which can be subsequently analysed by means of mass spectrometry technique. As an example, according to the prior art, a GC-MS analysis apparatus for analysing mixtures of gaseous substances can comprise a sampling cell, or "sample loop" from which the gaseous mixture sample can be taken by a carrier gas; a sample valve adapted for sampling a precise volume of the gaseous mixture; a separation assembly and a detector.

The chromatographic column is subjected to a temperature variation schedule in order to achieve the separation of the components of the substances passing through the same column and analyzing when they come out from the column. For this reason the column is generally accommodated inside a controlled temperature oven. Nitrogen ($N_2$), helium (He), or hydrogen ($H_2$) can be used as a carrier gas.

The detector can be, for instance, a flame ionization detector (FID) associated to an electrometer converting the current collected by the FID in a voltage signal, which originates a chromatogram.

With reference to FIG. 1, a GC-MS analysis apparatus according to the prior art is schematically shown, which is provided with a gas chromatograph GC and a section MS. In the illustrated example, the section MS is equipped with an electronic impact (EI) ionic source and the analysis part is obtained by means of a quadrupole analyser. Other commonly used types of analyser can comprise magnetic sectors or an ionic trap.

An electronic impact (E.I.) ionic source (11), provided with an ionization filament (15), is associated to an outlet aperture (17) of a chromatographic column (19) into which the analyte is entered. The column (19) is usually accommodated inside a temperature controlled oven (25). An injector device (21) is provided at the inlet of the column (19) in order to bring the substance, which is to be analysed into the gas chromatograph and which has preliminarily rendered a solution by using an appropriate solvent.

The chromatographic column (19) generally consists of a capillary tube made of silica glass and typically having an inner diameter smaller than 1 mm, for example in a range between 220 and 250 μm, and a length higher than 10 m, for example in a range between 10 and 60 m.

A carrier gas (G1), for instance He, $N_2$, $H_2$, Argon is used for carrying into the column (19) the substance to be sampled. Other gases (G2), for instance methane ($CH_4$), can be used for the chemical ionisation and sent to the ionic source (11) through an appropriate conduit (27). The analyte passes through the column (19), comes out from the aperture (17) and is ionised at the ionic source (11) accommodated in a first section S1 of the apparatus. At the exit of the ionic source (11) an ionic guide (35) is further provided, which is made of an electrostatic lens having the purpose to convey the ions to the subsequent section.

Downstream of the guide (35) a second ionic guide (37), for example a radio frequency hexapole or an octopole or miniquad, is generally positioned, through which the ionic beam is transmitted to a second section S2 of the apparatus, which is provided with a third ionic guide (39) and a quadrupole analyser (41). The sections S1 and S2 of the apparatus are accommodated inside a casing (23) and separated by a septum (46) having an orifice or "skimmer" (48).

The detector (43) is located downstream of the quadrupole (41) and is generally made of dynodes, namely electronic multipliers which are capable of amplifying the very low current produced by the ions which have passed the analyser. Examples of known detectors are Faraday cup detectors, SEM (Second Electron Multiplier) detectors and Channeltron detectors.

The described example relates to a "single quad", however other devices and other quadrupoles can be provided along the path followed by the analyte and other quadrupoles, such as, for example, a collision reaction cell for removing interferences.

This kind of known apparatus is generally equipped with vacuum pumps (45, 47), for instance a pair of turbomolecular vacuum pumps, generally provided with corresponding mechanical "pre-vacuum" pump in order to generate vacuum conditions, for instance of $10^{-3}$ mbar ($10^{-1}$ Pa) in the first section S1 and $10^{-5}$ mbar ($10^{-3}$ Pa) in the second section S2 of the apparatus.

The GC-MS apparatuses are now broadly used in several fields of technology, but their use is becoming more and more widespread. Apparatuses of this kind are used for analysing volatile substances, e.g. for quantifying contaminants in the pharmacological and forensic field, and for analysing hazardous wastes, the quality of industrial products, the presence of organic pollutant in environmental samples, and the presence of undesired substances in the food. The known apparatuses are complicated and expensive to manufacture and to manage, and require remarkable investments. The supply of the carrier gas and other gases are added costs. Therefore, the need of having simplified GC-MS analysis apparatuses is highly felt.

Calibrated leak devices are also known in the art. Devices of this kind allow for generating controlled gas flows through the membrane as well as to quantificate leakages value by calibrating the instruments required to detect them during tight tests. The currently used devices are substantially of two kinds: orifice leaks, or capillary, and helium permeation leaks. The first ones, also called pinholes, are generally made by laser ablation or chemical etching. Such technologies enable apertures to be manufactured with high precision and reproducibility. An example of the first kind of devices having membranes with nanoholes, passing through the membrane and having a nanometric size diameter, is disclosed in the US patent publication no. 2006/0144120. Devices of this kind allows for generating controlled gas flows through the membrane as well as to quantificate leakages values, by calibrating the instruments required to detect them, during tight tests. Another example of this kind of membrane is disclosed in WO 03/049840.

The permeation leaks devices have, a very unstable behaviour when the temperature changes (their value varies of about 3% per centigrade grade in case of temperature values around room temperature), have long response times, are fragile (being made of glass, they are easily breakable even when they only fall to the ground), are only available for helium, and have a single flow value. Examples of such devices are described in DE 195 21 275 and WO 02/03057. Gas sampling devices based on permeation leaks are also disclosed in U.S. Pat. No. 4,008,388, US publication no. 2002/134933, U.S. Pat. No. 4,311,669, U.S. Pat. No. 4,712, 008 and WO 2008/074984.

Selectively permeable membranes used in the field of mass spectrometry are also disclosed in U.S. Pat. No. 4,551,624 and Maden A M et Al: "Sheet materials for use as membranes in membrane introduction mass spectrometry" Anal. Chem., Am. Chem. Soc., US vol. 68, no. 10, 15 May 1996 (1996-05-15). Pages 1805-1811, XP000588711 ISSN:0003-2700.

Nanoholes membranes of the above first species have not to be confused with gas permeable membranes. Membranes of the first kind have holes made artificially, e.g. by laser drilling, having substantially regular cross section along the whole length of the hole and for this reason can be calibrated according to the use of the membrane; in addition, several or many almost identical holes with parallel axis can be produced on the same membrane. On the contrary, gas permeable membranes are membranes whose natural property of the material allows permeability of a gas or a gas mixture usually at a high temperature.

An object of the invention is to provide a simplified GC-MS apparatus, in particular with regard to the mechanical features and vacuum system, wherein the performances thereof are comparable with the ones of known apparatuses of the same category.

A further object of the invention is to provide an apparatus of the above specified type, which can be industrially mass produced with affordable costs.

Yet another object of the invention is to provide a GC-MS analysis apparatus, which is easier to manage with respect to the known ones having similar performances, and which therefore permits to reduce the maintenance costs.

These and other objects are achieved by means of a GC-MS apparatus as claimed in the appended claims.

SUMMARY OF THE INVENTION

The invention, which will be described as follows, is not limited to one particular category of GC-MS analysis apparatuses and the references to the known apparatuses previously described have been provided purely by way of example.

Advantageously, the interface section according to the present invention determines the necessary analyte molecular flow directed towards the section MS and the pumping capability required for the vacuum system can therefore result to be reduced with respect to the prior art devices, wherein substantially the whole flow coming from chromatographic column is sent to the MS section. This condition makes possible, for example, use of ionic vacuum pumps, which are, in general, structurally more simplified than vacuum systems based on turbomolecular pumps having a rotary mechanical structure and requiring complicated electronic control devices. Due to the vacuum system simplification, the consequent reduced weight and the lower electrical current absorption, it is advantageously possible to manufacture apparatuses, which are compact, transportable and battery-operated.

The apparatus according to the invention advantageously incorporates at least one membrane having at least one nanohole, with an orifice having nanometric size with diameters comprised between 10 nm and 500 nm, thereby determining a controlled analyte flow directed towards the ionic source in the section MS and a consequent lower pumping demand from the vacuum pumps with which the section MS is equipped.

The membrane is substantially impermeable to the gas flow but that through the nanohole or nanoholes and preferably comprises only one nanohole or a limited number of nanoholes, more precisely from ten to hundred nanoholes.

The selection of a membrane having at least one nanohole, or nanoholes, of the type wherein the diameter D and the length L of the nanohole, or nanoholes, are dimensioned so as L<20·D, and wherein the equivalent diameter De of the orifice is De≦100 nm, where De is defined by the relation $De = D \cdot a^{1/2}$, where a is the transmission probability of the orifice, which is function of the L/D ratio, determines a remarkable reduction in the nanoholes tendency to get clogged.

BRIEF DESCRIPTION OF THE DRAWINGS

Some embodiments of the present invention will be described as follows purely by way of example with reference to the drawings wherein.

In all the drawings, the same numerical references have been used to denote the same, or functionally equivalent, components.

DESCRIPTION OF THE PREFERRED EMBODIMENTS

Figure 2A:
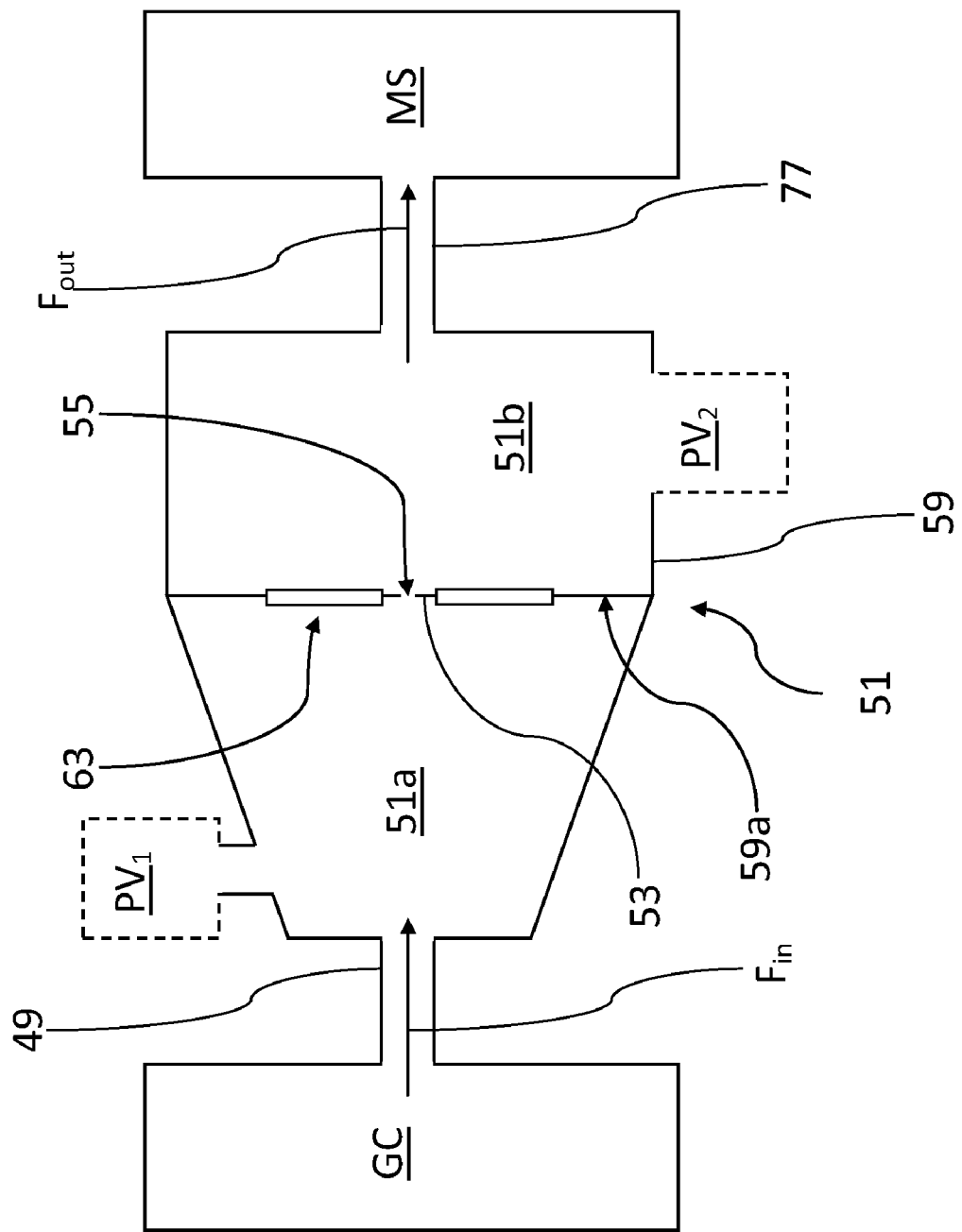
FIGS. 2A and 2B are block diagrams of an apparatus according to a first and modification embodiments of the present invention, respectively.

With reference to FIG. 2A, the GC-MS apparatus according to a first embodiment of the invention comprises a gas chromatographic section GC and a spectrometric analysis section MS. Advantageously, according to the invention, these two sections are respectively associated through an interface section, which is overall denoted by the reference 51 and which is located downstream of the section GC and upstream of the section MS, taking as a reference the preferred path direction followed by the analyte into the apparatus and indicated in the FIG. 2A with the arrows $F_{in}$ and $F_{out}$.

According to the present invention, the interface section 51 comprises at least a membrane 53 having at least one orifice 55 capable of establishing a molecular flow condition in the analyte passing from the section GC to the section MS through the orifice 55, when the membrane 53 is subjected to a pressure differential such that the pressure $p_a$ in the region 51a located upstream of the membrane 53 is higher than the pressure $p_b$ in the region 51b located downstream of the membrane 53. Preferably the order of magnitude of the pressure differential is at least one and, more preferably, is two or more.

In an exemplary embodiment, the region 51a has been maintained at a pressure of about the atmospheric pressure of 1 bar ($10^5$ Pa), and the region 51b at a pressure comprised between about $10^{-2}$ mbar (10 Pa) and $10^{-7}$ mbar ($10^{-5}$ Pa). Pressures exceeding the atmospheric pressure in the region 51a are also feasible.

According to a preferred embodiment of the invention, at least one orifice 55 consists of a nanohole, a hole passing through the membrane 53 and having a diameter D being of nanometric size and preferably in a range between 10 nm e 500 nm. The orifice 55 can be of any shape, but the circular shape is generally the easiest to obtain. Moreover the membrane 53 is preferably planar and the orifice 55 develops through the membrane 53 around an axis, which is substantially perpendicular with respect to the surface of the membrane 53, and has a substantially uniform transverse section.

Furthermore, always according to the invention, the orifice preferably has a diameter D and a length L such that L<20·D. Even more preferably the membrane 53 is of the type wherein the diameter D and the length L are dimensioned so that the equivalent diameter $D_e$ of the orifice is $D_e \leq 100$ nm, where $D_e$ is defined by the relation $D_e = D \cdot a^{1/2}$, where a is the transmission probability of the orifice which is a function of the L/D ratio. The latter condition has proved to be especially effective in order to avoid the obstruction "clogging" of the nanohole due to, for example, impurities.

Furthermore the interface section 51 can advantageously have, depending on the use, one only membrane 53 with more than one nanohole 55, namely with a plurality of nanoholes 55, or more membranes, which can also be respectively different and provided with any number of nanoholes. The nanoholes can further have different sizes. Preferably, according to the present invention, the region 51a and 51b of the interface section communicate one with the other exclusively through the nanohole or nanoholes 55 of the membrane or membranes 53, which separate or separate the two spaces.

The membrane 53 can be advantageously made of a ceramic, metallic, semiconductor material or a combination thereof, and the orifice 55 can be obtained by means of an erosion process, (by means of a highly focused ion beam in accordance to the technique FIB (Focused Ion Beam)).

In a preferred embodiment of the present invention, the membrane 53 is accommodated into a hermetic vacuum tight casing 59 into which the analyte coming from the section GC of the apparatus enters (direction shown by the arrow $F_{in}$) for instance through a duct 49, and from which the analyte with a molecular flow comes out (direction shown by the arrow $F_{out}$) through the membrane 53 towards the section MS, e.g. by passing through a passage 77. More precisely, the membrane 53 is located inside the casing 59 so as to define at the interior thereof two spaces 51a, 51b which communicate one with the other through the nanohole 55 of the membrane 53 or, in other embodiments of the invention, through the plurality of nanoholes provided in the same membrane or also through nanoholes distributed in a plurality of membranes.

Optional draining and/or recycling means, comprising appropriate vacuum pumps $PV_1$ and $PV_2$ and/or the same vacuum pumps with which the sections GC and MS are equipped, consent to generate, between said space 51a located upstream of the membrane 53 and the space 51b located downstream of the membrane, the necessary pressure differential and to cause the molecular flow of the analyte through the nanohole or nanoholes in the direction indicated with the arrows $F_{in}$ and $F_{out}$ in the FIG. 2A.

According to the invention, the membrane 53 can be directly associated, by means of vacuum-tight gluing, to a septum 59a extending inside the casing 59 between the spaces 51a and 51b, at an aperture provided therein which is therefore completely engaged by the membrane 53. As an alternative, the membrane 53 can be accommodated in a support 63, which will be further described in more detail and the support 63 can be fixed e.g. welded or glued in a vacuum tight manner, to the septum 59a so as to engage the aperture provided therein for such purpose.

Figure 3:
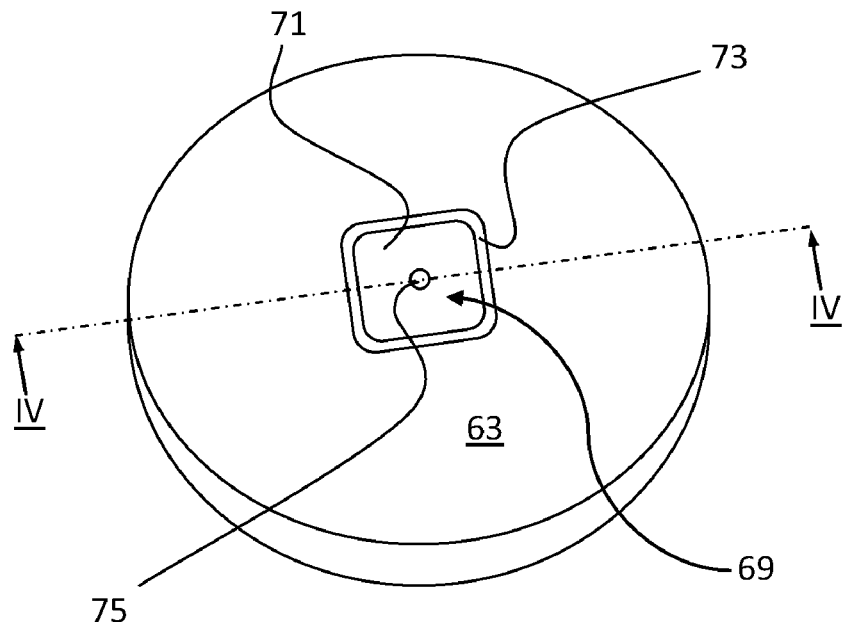
FIG. 3 is a perspective view of the support adapted for the interface membrane.
Figure 4:
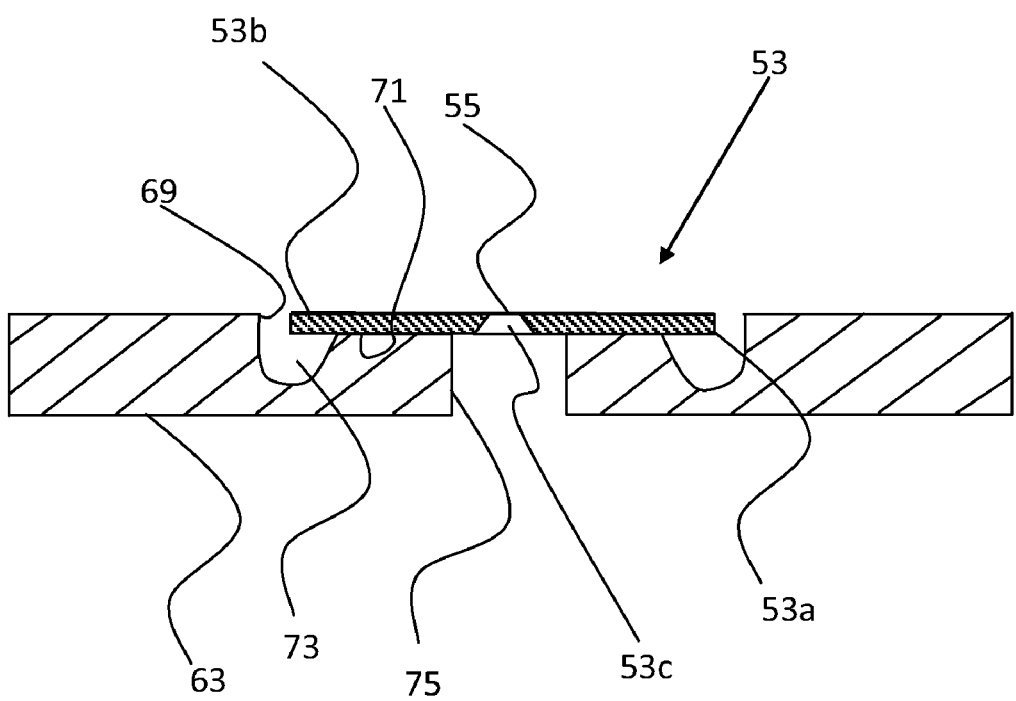
FIG. 4 is a section view taken along the line IV-IV indicated in FIG. 3.

With reference to FIGS. 3 and 4, in a preferred embodiment of the invention, the membrane 53 comprises a substrate 53a made of silicon (Si) and a surface cover layer 53b in silicon nitride (SiN). According to the preferred invention, the layer 54b made of silicon nitride is preferably faces the space 51a having higher pressure $p_a$, while the substrate 53a faces the space having lower pressure $p_b$. In an exemplary embodiment of the membrane 53, the substrate 53a and the layer 53b had a thickness of about 0.1-0.3 mm and respectively 200 nm. Always according to the invention, the membrane 53, in particular the face of the layer 53b, which is turned towards the space 51a having higher pressure, can further be subjected, depending on the requests, to surface coating treatments such as applying a waterproof coating, in order to avoid the water vapour generation, which could contribute to cause the clogging, namely the obstruction of the nanohole or nanoholes and consequently the interruption or reduction of the molecular flow of the analyte passing from the section GC to the section MS.

In other embodiments, the membrane 53 can advantageously be associated with heating means, which are still provided in order to avoid clogging risks. The membrane 53 is preferably accommodated in a support 63 advantageously provided with an appropriate well 69, wherein the membrane 53 can be housed. Furthermore the support 63 is preferably made of metal, e.g. copper. The support 63 can have, for example, a disc-like shape having a diameter comprised between about 20 mm and 25 mm and a thickness comprised between about 1.5 mm ad 2.5 mm. In the illustrated example, the well 69 is substantially defined at the centre of the support 63 and is a square, seen according to a plan view, into which a membrane 53 having preferably a complementary shape can be accommodated. In this exemplary embodiment, the membrane 53 can be for example a square, seen according to a plan view, having a side comprised between about 3.0 e 8.0 mm and a thickness of about 0.20, and the well 69 can have a side length comprised between 5.0 and 10.0 mm.

Moreover the well 69 further comprises a bearing zone 71 for the membrane 53, preferably located in a central position and situated at a slightly lowered height with respect to the surface of the support 63, so that when the membrane 53 rests on the zone 71. The perimeter edges of the well 69 prevent the lateral escape of the membrane, thereby facilitating the mounting thereof. In other words, it is sufficient that the perimeter sides of the well 69 determine a holding perimeter for the membrane 53 when this rests on the central zone 71.

The bearing zone 71 of the support 63 is further surrounded by a channel 73, in which an adhesive substance, e.g. a sealing resin, can be distributed in order to hold the membrane 53 on the support 63. The holding perimeter defined by the perimeter edges of the well 60 is further preferably spaced from the sides of the membrane 53 in order to allow the adhesive to flow out from the channel 73 when the membrane 53 is located on the bearing zone 71 and to adhere a perfect adhesion of the membrane 53 to the support 63. Advantageously, the channel 73 can be obtained by means of mechanical machining or by means of electrical discharge machining or laser ablation, so as to make preferably the inner surface to be rough in such a manner to guarantee the optimal adhesion of the adhesive material distributed thereon. The bearing surface 71 of the support 63 further comprises an aperture 75 located at the nanohole 55 provided in the membrane 53. If the membrane 53 had more than one nanohole, the aperture 75 is provided with a size and/or a number which is/are adequate for not obstructing the nanoholes.

In the exemplary embodiment shown, the nanohole 55 is advantageously made at a thinner central zone 53c of the membrane 53, wherein the substrate 53a has been removed and remains only the layer 53b. The thinner zone is, for example, substantially square with a side comprised between 20 and 500 micron. Other embodiments are however possible wherein the nanohole or nanoholes 55 are made in the membrane 53, without removing the substrate 53a or by removing it only partially. According to the invention, the nanohole or nanoholes in the membrane 53 are made only in the layer 53b or in both the layer 53b and the substrate 53a. Moreover, according to the invention, the support 63, the respective well 69 and the membrane 53 can assume substantially any shape, e.g. circular, square, rectangular, rhombus-like, irregular, etc., according to the needs.

Figure 2B:
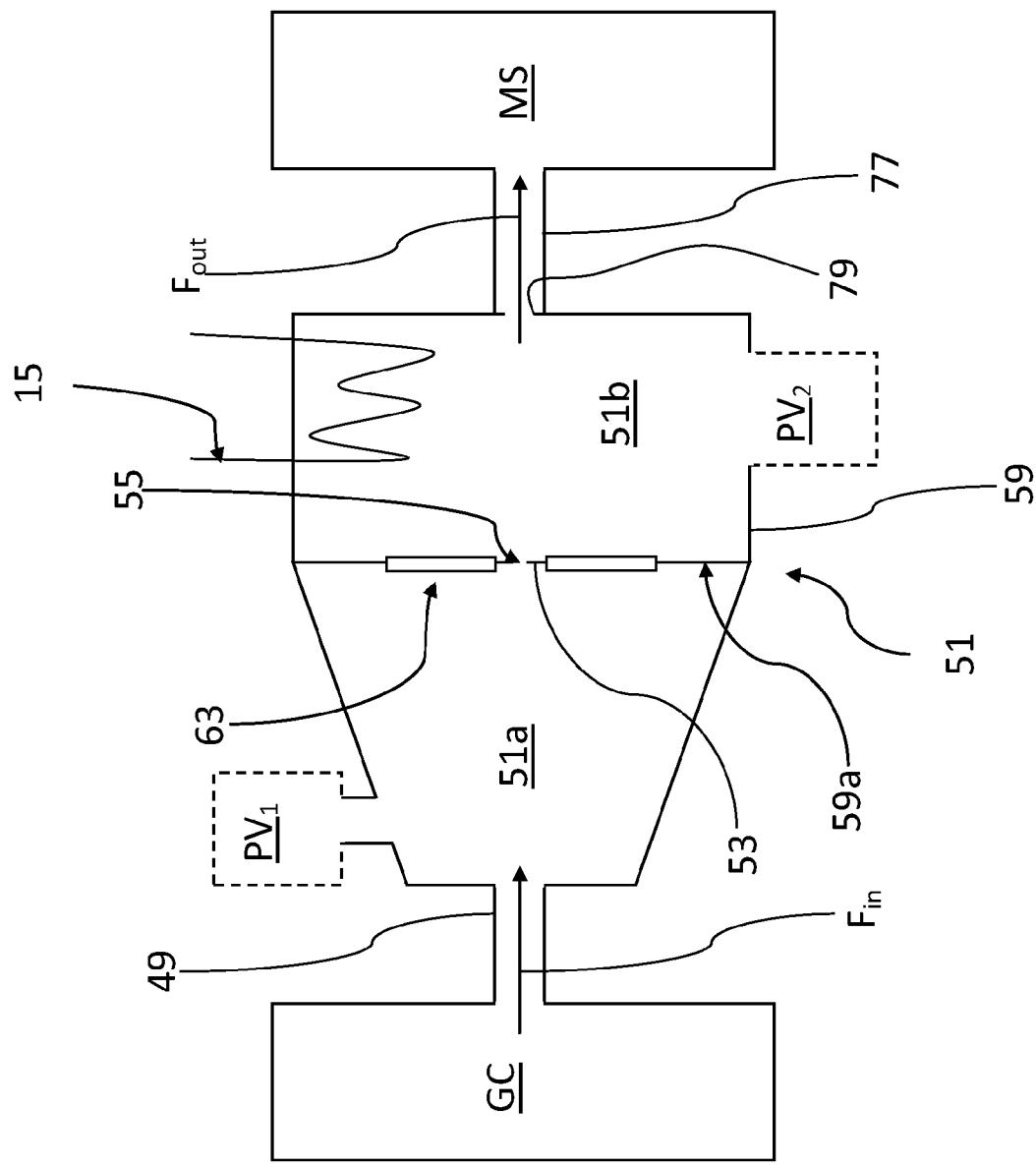

With reference to FIG. 2B the ionic source is substantially integrated in the space 51b of the interface section 51, with a consequent reduction of the components in the apparatus. If the ionic source is of the electronic impact (EI) type, the membrane 53 and the respective possible support 63 are appropriately configured for resisting to the temperatures reached in the ionic source, caused by the heating up of the incandescence of the filament 15 and can reach high values of some thousand Celsius degrees.

With reference to both FIGS. 2A and 2B, as it is known, the conductance C of a hole with a diameter having nanometric size (~100 nm), which separates two spaces maintained in differential vacuum condition, can be measured, at the atmospheric pressure or at a lower pressure, as $$C = \left(\frac{1/4 \cdot (8 \cdot R \cdot T)}{\pi \cdot M}\right)^{1/2} \cdot A \quad (1)$$

where A is the hole surface, T is the gas temperature, R is the gas constant, and M is the gas mass.

The concentration which the gas mixture has during the passage from the region 51a to the space 51b through the membrane 53 is therefore subjected to a change according to the formula shown above (increasingly lighter gases have an increasingly higher concentration in the region 51b). Through the membrane 53 there is however a molecular regime, and at a ionic outlet calibrated hole 79 directed to the section MS there is a molecular regime flow adjusted again according to the same formula (increasingly lighter gases come out in an increasingly higher extent). Overall, by appropriately defining the size of the hole 79, the same concentration of the various gasses, which make up the gas mixture coming from the section GC can therefore be restored inside the space 51b.

The hole 79 has generally a diameter in order of millimeters, preferably comprised between 1 and 10 mm, e.g. 2.5 mm, and a length within millimeter, e.g. 1 mm. Values lower than 1 mm are however possible, for instance 0.5 or 0.1 mm. Moreover, in order to achieve the desired flow, a plurality of calibrated holes 79 can be also provided.

Clearly, a similar calibrated hole 70 can be advantageously provided even in the first embodiment of the invention, shown in FIG. 2A. In such case the calibrated hole 79 is provided at the outlet of the ionic source with which the section MS is equipped.

Figure 1:
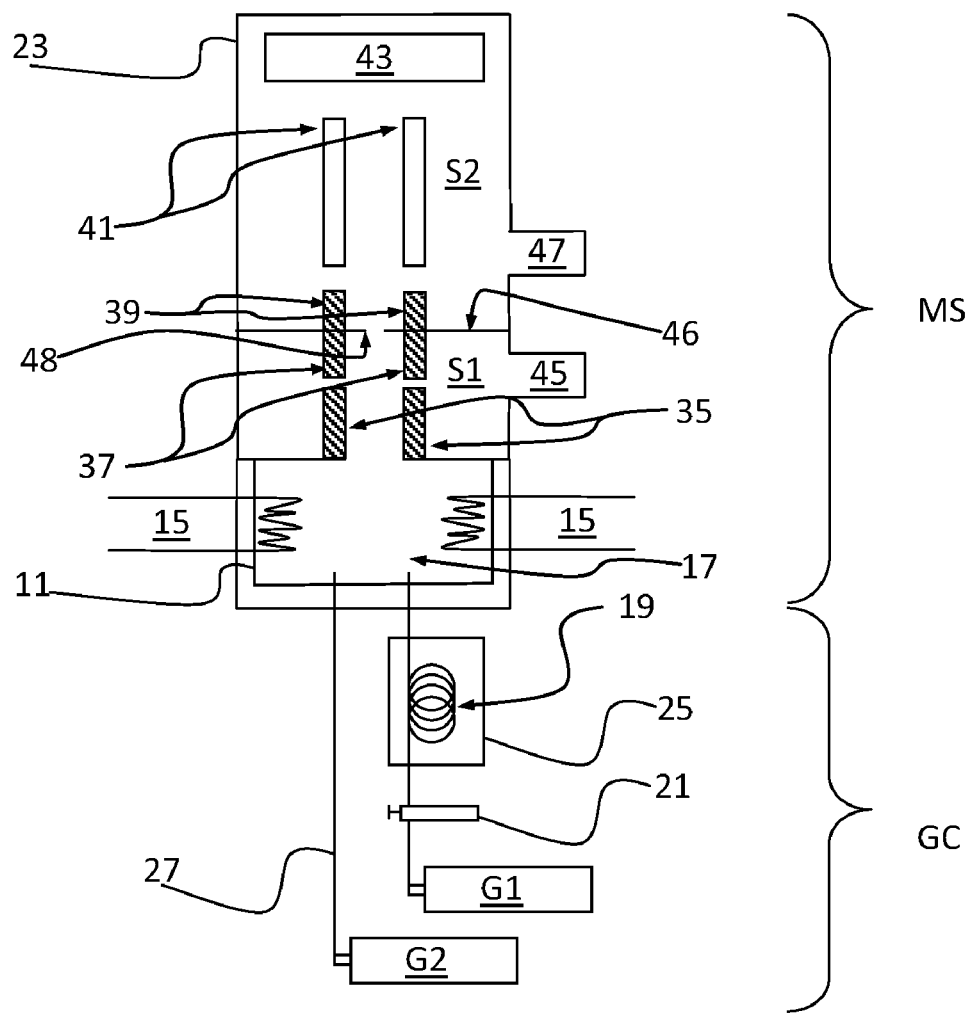
FIG. 1 is a schematic example of a GC-MS apparatus according to the prior art.

As a first example of industrial use for the invention, reference will be made to FIG. 5 wherein a "single quad" GC-MS apparatus is shown, which is substantially made according to the scheme previously described with reference to FIG. 1 and in which an interface section 51 has been integrated according the first embodiment shown in FIG. 2A. This apparatus is mainly provided with a chromatographic column 19, an electronic impact ionic source 11, a quadrupole analyser 41, and a detector 43. The chromatographic column 19 of the section GC is associated to the casing 59 of the interface section 51 in such a manner that the exit aperture 17 of the column 19 is in communication with the interface section 51 and, more precisely, with the space 51a located upstream of the membrane 53.

The space 51b located downstream of the membrane 53 inside the casing 59 communicates with the section MS by coming into the ionic source 11 in a direct manner or, as in the example shown, through an appropriate passage 77. In this embodiment, at the space 51a of the interface section 51, a recycle vacuum pump $PV_1$ is provided. The vacuum pump $PV_1$ can, for instance, comprise a membrane vacuum pump capable of draining the space 51a in order to generate inside it the desired pressure, e.g. about 1 bar ($10^5$ Pa) or more, which is necessary, for example, to recycle the solvent.

According to this embodiment, in the space 51b located downstream of the membrane 53, the necessary vacuum degree, typically about $10^{-5}$ mbar ($10^{-3}$ Pa) is instead obtained directly by means of the possible pump 47, preferably omitting the septum 46 and the respective orifice or "skimmer" 48 and without needing the pump 45, or by means of the possible pump 45 with which the section S1 of the section MS is equipped, the space 51b being in communication with the ionic source 11 through the passage 77.

According to the present invention, due to the presence of the interface section having a membrane with a nanoholes (nanoholes), which determines an analyte molecular flow directed to the section MS and extremely reduced with respect to the prior art, the vacuum pump or the vacuum pumps with which the section MS is equipped can be, for example, of the ionic type, namely more simple than the generally used turbomolecular pumps, the required pumping capacity being remarkably lower than in the devices according to the prior art wherein substantially all the analyte flow coming from the chromatographic column is sent to the section MS.

Figure 5:
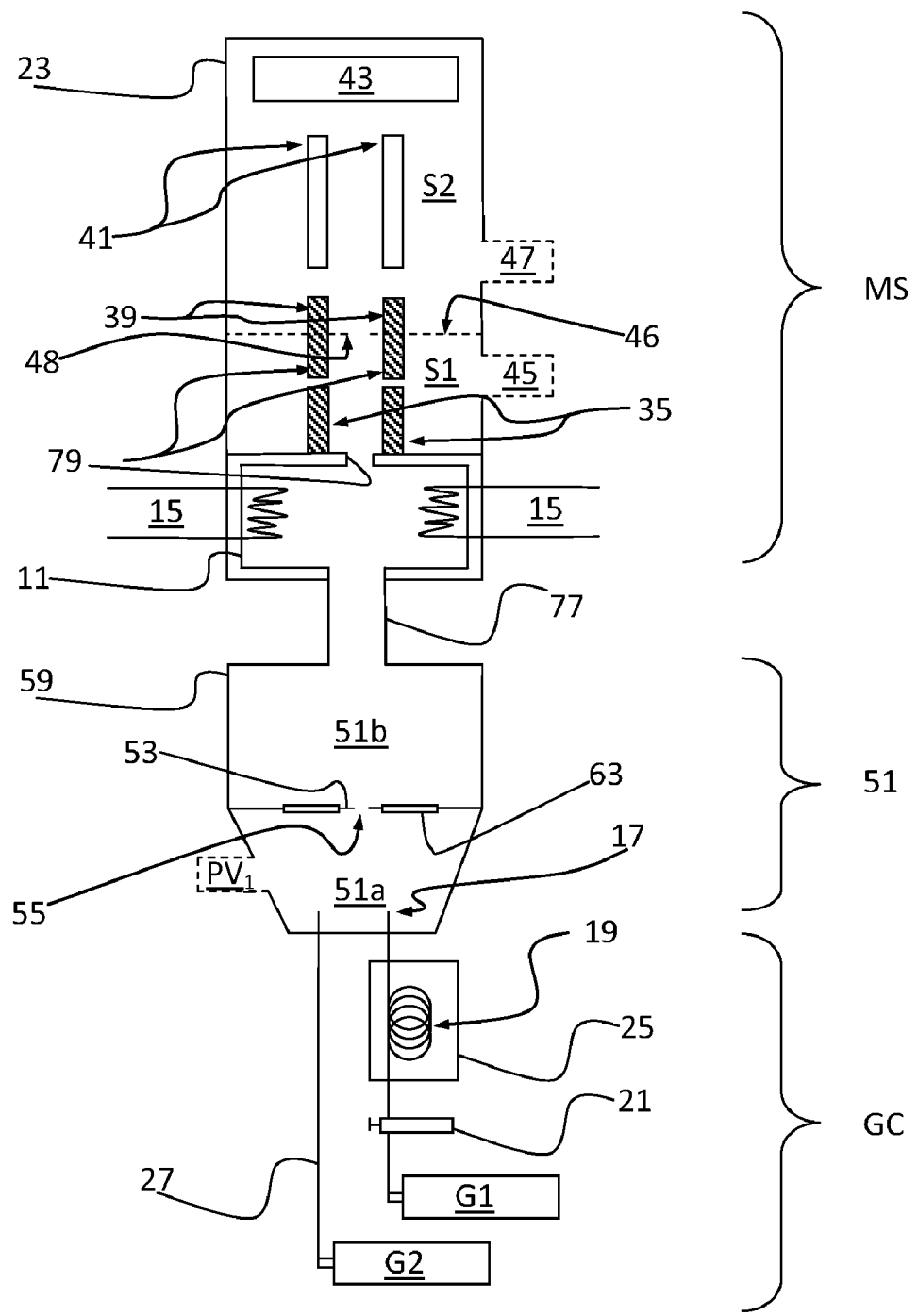
FIG. 5 illustrates the apparatus of FIG. 1, into which the embodiment of FIG. 2A of the present invention is integrated.

With reference again to the embodiment of FIG. 5, the calibrated hole 79 is preferably provided at the outlet of the ionic source 11 in order to maintain a ionic flow in a molecular regime, which is adjusted again by the same above cited formula 1 (increasingly lighter gases come out in an increasingly higher extent).

It can be noticed that even if the passage 77 had such a small size to determine a pressure variation between the space 51b and the ionic source 11, the above cited condition (namely, in the space 51b there is the same concentration distribution in the various gases which make up the gas mixture coming from the section GC) would be always guaranteed by the presence of the calibrated hole 79, though an ionic flow would be always maintained in an adjusted molecular regime.

Figure 6:
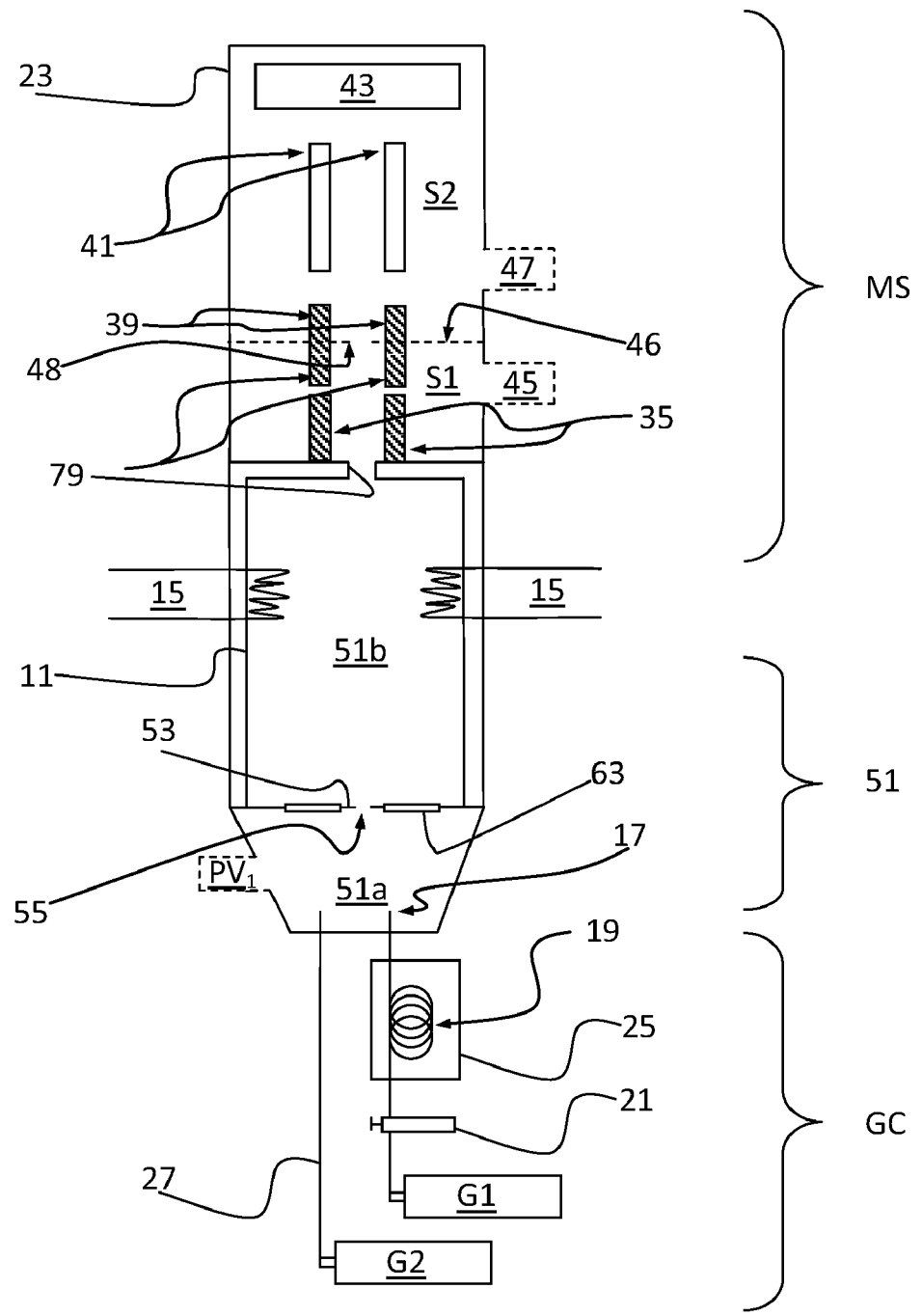
FIG. 6 illustrates the apparatus of FIG. 1, into which the embodiment of FIG. 2B is integrated.

As a second example of industrial use for the invention, reference will be now made to FIG. 6, wherein a GC-MS apparatus is shown which is substantially made according the scheme previously described with reference to FIG. 1 and in which an interface section 51 according to the embodiment shown in FIG. 2B is integrated. This apparatus is mainly provided with a chromatographic column 19, an electronic impact ionic source 11, a quadrupole analyser 41, and a detector 43. According to this embodiment, the membrane 53 is associated to the interior of the ionic source 11 in a direct manner or by means of an appropriate support 63. The ionic source is therefore integrated in the space 51b of the interface section 51 or, vice versa, the space 51b is integrated in the ionic source 11, with a consequent reduction of the components in the apparatus. According to this embodiment, the membrane 53 and the respective support 63 are appropriately configured for resisting to the temperatures reached in the ionic source and due to the heating up the incandescence of the filament 15.

Although the present invention has been described with particular reference to a Single-Quad GC-MS device of the type provided with a chromatographic column, an electronic impact ionic source, and a single quadrupole (Single Quad) analyser, however the described interface section can advantageously be integrated in any GC-MS apparatus.

For example, the invention can be used in GC-MS apparatuses provided with a ionic source which is different from the electronic impact ionic source, such as FAB (Fast Atom Bombardment), Chemical Ionization, Laser Ionization.

Furthermore, the invention can advantageously be used in GC-MS apparatuses which include magnetic analysers, triple quadrupole (Triple Quad) analysers, TOF ("time of flight") analysers, ion-trap analysers, Omegatron analysers, wherein the mass selection can be performed by using a magnetic field and an RF field, FT-ICR (Fourier Transform Ion Ciclotron Resonance) analysers, cycloidal mass analysers (the mass selection is made by an appropriate selection of the resultant magnetic and electric field), magnetic section analysers and ionic trap analysers.

What is claimed is:

1. A GC-MS analysis apparatus comprising:
    a gas chromatographic (GC) section and a spectrometric analysis (MS) section; and
    an interface section associated with the GC and the MS and located with respect to a flow of analyte downstream of the GC section and upstream of the MS section,
        said interface section comprising at least one membrane with at least one orifice capable of establishing a molecular flow condition in the analyte flowing from said GC section through said membrane to said MS section while said membrane is subjected to a pressure differential when pressure $p_a$ in an upstream region of the membrane is higher than pressure $p_b$ in a downstream region of the membrane.

2. Apparatus according to claim 1, wherein said orifice is a nanohole being a hole passing through the membrane and having a diameter measured in nanometers.

3. Apparatus according to claim 2, wherein said nanohole has a diameter D in a range between 10 nm and 500 nm.

4. Apparatus according to claim 3, wherein the diameter D and a length L of the nanohole are dimensioned such that $L<20 \cdot D$.

5. Apparatus according to claim 4, wherein the diameter D and the length L are dimensioned so that an equivalent diameter $D_e$ of the orifice is $D_e \leq 100$ nm, where $D_e$ is defined by $D_e = D \cdot (a)^{1/2}$, where a is the transmission probability of the orifice, which is a function of the L/D ratio.

6. Apparatus according to claim 1, wherein the membrane is substantially planar and wherein said orifice develops through the membrane along an axis, which is substantially perpendicular with respect to the surface of the membrane and has a substantially uniform transverse cross-section.

7. Apparatus according to claim 1, wherein the interface section includes an ionic source and wherein said ionic source communicates with a space situated downstream through at least one calibrated hole.

8. Apparatus according to claim 1, wherein the interface section communicates with an ionic source and wherein said ionic source communicates with the space situated downstream through at least one calibrated hole.

9. Apparatus according to claim 8, wherein said calibrated hole has a diameter, which length is measured in millimeters or lower units.

10. Apparatus according to claim 1, wherein said GC section comprises at least one chromatographic column, an exit aperture of said column being in communication with said interface section.

11. Apparatus according to claim 1, wherein the MS section comprises an electronic impact ionic source and a quadrupole analyser.

12. Apparatus according to claim 1, wherein the membrane is accommodated into a well formed in a support and wherein the well comprises an aperture located at the orifice made in the membrane.

13. Apparatus according to claim 12, wherein the well further comprises a bearing zone for the membrane locating at a height that is slightly lower with respect to a surface of the support, wherein perimeter edges of the well prevent the membrane to escape when resting on the bearing zone.

14. Apparatus according to claim 13, wherein a resting zone of the support for the membrane is surrounded by a channel comprising an adhesive substance for holding the membrane in the support.

15. Apparatus according to claim 1, wherein said membrane comprises from one nanohole to hundred nanoholes and wherein said membrane is substantially impermeable to the gas flow except through said nanohole or nanoholes.

* * * * *